United States Patent
Ringermacher et al.

(10) Patent No.: US 6,367,968 B1
(45) Date of Patent: Apr. 9, 2002

(54) THERMAL RESONANCE IMAGING METHOD

(75) Inventors: Harry I. Ringermacher, Delanson; Donald R. Howard, Troy, both of NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/568,052

(22) Filed: May 10, 2000

Related U.S. Application Data
(60) Provisional application No. 60/144,885, filed on Jul. 21, 1999.

(51) Int. Cl.$^7$ .............................................. G01N 25/72
(52) U.S. Cl. ............................ 374/7; 374/5; 250/341.6; 250/330
(58) Field of Search ...................... 374/4–7; 250/341.6, 250/330, 332

(56) References Cited

U.S. PATENT DOCUMENTS

| | | |
|---|---|---|
| 4,768,158 A | 8/1988 | Osanai |
| 4,792,683 A | 12/1988 | Chang et al. |
| 4,854,724 A | 8/1989 | Adams et al. |
| 5,032,727 A | 7/1991 | Cox, Jr. et al. |
| 5,201,582 A | * 4/1993 | Lesniak ....................... 250/332 |
| 5,246,291 A | 9/1993 | Lebeau et al. |
| 5,250,809 A | 10/1993 | Nakata et al. |
| 5,292,195 A | 3/1994 | Crisman, Jr. |
| 5,539,656 A | 7/1996 | Annigeri et al. |
| 5,582,485 A | 12/1996 | Lesniak |
| 5,631,465 A | 5/1997 | Shepard |
| 5,683,181 A | 11/1997 | Shepard |
| 5,711,603 A | 1/1998 | Ringermacher et al. |

FOREIGN PATENT DOCUMENTS

| | | |
|---|---|---|
| EP | 304 708 | 3/1989 |
| GB | 2 168 494 | 6/1986 |
| GB | 2 220 065 | 12/1989 |
| JP | 10 274 675 | 10/1998 |
| WO | 98/05921 | 2/1998 |
| WO | 98/05949 | 2/1998 |

OTHER PUBLICATIONS

Article entitled "Thermal NDE System", Aerospace Engineering, Oct. 1995, p. 7.

(List continued on next page.)

Primary Examiner—Diego Gutierrez
Assistant Examiner—Stanley J. Pruchnic, Jr.
(74) Attorney, Agent, or Firm—Nixon & Vanderhye PC

(57) ABSTRACT

In an infrared (IR) transient thermography system a sequence of image frames is acquired from an IR sensitive focal-plane array camera. Each sequentially acquired image frame is made up of an array of pixels and has assigned a frame-number that corresponds to elapsed time. Temperature-versus-time (T-t) data corresponding to each pixel is developed from stacks of sequential image-frames. A method of analyzing the stacks of thermal data image-frames is presented wherein either the Real or the Imaginary component portions of a Fast-Fourier Transform of a normalized T-t data curve from each pixel is used to determine the thickness of an object and produce a color-keyed or gray-scale coded thickness map.

18 Claims, 3 Drawing Sheets

OTHER PUBLICATIONS

Article entitled "Thermal Evaluation Reveals Depth Detail", Photonics Spectra, Jun. 1995, pp. 21–22.

Ringermacher, H.I. et al., "Towards a Flat–Bottom Hole Standard for Thermal Imaging", Review of Progress in Quantitative Nondestructive Evaluation, vol. 17A, Edited by D.O. Thompson and D.E. Chimenti, Plenum Press, New York, May 1998, pp. 425–429.

Milne, J. M., et al., "The non–destructive evaluation of composites and other materials by thermal pulse video thermography", SPIE vol. 520 Thermosense VII (1984), pp. T–15–T–18.*

Becker et al., "Method of Determining The Wall Thickness of a Turbine Blade and Device for Carrying out This Method", English Translation (PTO 01–927) of WO 98/05921 A1, Feb. 1998.*

* cited by examiner

THERMAL RESONANCE IMAGING METHOD

This application claims the benefit of U.S. Provisional Application No. 60/144,885, filed Jul. 21, 1999 the entire content of which is hereby incorporated by reference in this application.

TECHNICAL FIELD

The present invention relates to thermographic nondestructive testing techniques for determining the thickness of an object. More particularly, the present invention relates to a infrared transient thermography method for analyzing stacks of thermal data image-frames that employs a Fast-Fourier Transform thermal resonance function to determine thickness.

BACKGROUND

Over the years, various nondestructive ultrasonic measurement techniques have been utilized to determine cross-sectional thickness of cast metal and other solid objects. Conventionally, the object is probed with ultrasonic waves which penetrate the surface and are reflected internally at the opposite side or surface of the object. Based upon the time required to receive a reflected wave, the distance to the opposite (back) side can be determined—giving the thickness of the object at that point. Unfortunately, conducting ultrasonic measurements of this sort to examine the cross-sectional thickness for most of an object would usually necessitate a cumbersome and time-consuming mechanical scanning of the entire surface with a transducer. In addition, to facilitate intimate sonic contact between the transducer and the object surface, a stream of liquid couplant must be applied to the surface or, alternatively, total immersion of the object in the couplant must be accommodated. Such accommodations, however, are most often not very practical or even feasible for numerous structural and material reasons. For example, ultrasonic systems capable of scanning and analyzing geometrically complex parts are typically very expensive and complicated. In addition, a mechanical scanning of the transducer over the surface of a large object can literally take hours.

Moreover, when conducting ultrasonic measurements on certain metal objects, the internal crystal orientation and structure of the metal can cause undesirable noise and directional effects that contribute to inaccuracies in the acquired data. This inherent limitation of ultrasonic measurements proves to be a serious drawback when testing components constructed of crystalline or "directional" metals such as often used in contemporary turbine airfoils.

In contrast, infrared (IR) transient thermography is a somewhat more versatile nondestructive testing technique that relies upon temporal measurements of heat transference through an object to provide information concerning the structure and integrity of the object. Since heat flow through an object is substantially unaffected by the micro-structure and the single-crystal orientations of the material of the object, an infrared transient thermography analysis is essentially free of the limitations this creates for ultrasonic measurements. In contrast to most ultrasonic techniques, a transient thermographic analysis approach is not significantly hampered by the size, contour or shape of the object being tested and, moreover, can be accomplished ten to one-hundred times faster than most conventional ultrasonic methods if testing objects of large surface area.

One known contemporary application of transient thermography, which provides the ability to determine the size and "relative" location (depth) of flaws within solid non-metal composites, is revealed in U. S. Pat. No. 5,711,603 to Ringermacher et al., entitled "Nondestructive Testing: Transient Depth Thermography"; and is incorporated herein by reference. Basically, this technique involves heating the surface of an object of interest and recording the temperature changes over time of very small regions or "resolution elements" on the surface of the object. These surface temperature changes are related to characteristic dynamics of heat flow through the object, which is affected by the presence of flaws. Accordingly, the size and a value indicative of a "relative" depth of a flaw (i.e., relative to other flaws within the object) can be determined based upon a careful analysis of the temperature changes occurring at each resolution element over the surface of the object. Although not explicitly disclosed in the above referenced Ringermacher patent, the "actual" depth of a flaw (i.e., the depth of a flaw from the surface of the object) can not be determined unless a "standards block", having voids at known depths, or a thermally thick ("infinite half-space") reference region on the object is included as part of the thermographic data acquisition and analysis for comparison against the relative depth values.

To obtain accurate thermal measurements using transient thermography, the surface of an object must be heated to a particular temperature in a sufficiently short period of time so as to preclude any significant heating of the remainder of the object. Depending on the thickness and material characteristics of the object under test, a quartz lamp or a high intensity flash-lamp is conventionally used to generate a heat pulse of the proper magnitude and duration. However, the specific mechanism used to heat the object surface could be any means capable of quickly heating the surface to a temperature sufficient to permit thermographic monitoring—such as, for example, pulsed laser light. Once the surface of the object is heated, a graphic record of thermal changes over the surface is acquired and analyzed.

Conventionally, an infrared (IR) video camera has been used to record and store successive thermal images (frames) of an object surface after heating it. Each video image is composed of a fixed number of pixels. In this context, a pixel is a small picture element in an image array or frame which corresponds to a rectangular area, called a "resolution element", on the surface of the object being imaged. Since, the temperature at each resolution element is directly related to the intensity of the corresponding pixel, temperature changes at each resolution element on the object surface can be analyzed in terms of changes in pixel contrast. The stored IR video images are used to determine the contrast of each pixel in an image frame by subtracting the mean pixel intensity for a particular image frame, representing a known point in time, from the individual pixel intensity at that same point in time.

The contrast data for each pixel is then analyzed in the time domain (i.e., over many image frames) to identify the time of occurrence of an "inflection point" of the contrast curve data, which is mathematically related to a relative depth of a flaw within the object. Basically, as applied to an exemplary "plate-like" object of consistent material and thickness L, a migrating heat-flux pulse impinging on an object takes a certain "characteristic time", $T_C$, to penetrate through the object to the opposite side (back wall) and return to the front surface being imaged. This characteristic time, $T_C$, is related to the thickness of the object, given the thermal diffusivity of the material, by the following equation:

$$T_C = 4L^2/\pi^2 \alpha \qquad \text{EQU. 1}$$

where L is the thickness (cm) of the object and α is the thermal diffusivity (cm²/sec) of the material. (An object may also be thermally imaged from a side of the object opposite the heat-flux source. This merely results in a value of $T_C$ being different by a factor of four.)

From empirical observations it is known that after a heat pulse impinges on a plate-like object, the surface temperature observed from the same side of the object (i.e., the front) rises in a fashion that is also dependent on the thickness and the thermal diffusivity of the material. Moreover, from a graph of the temperature vs. time (T-t) history of the surface, one can determine the characteristic time, $T_C$, in terms of a unique point on the T-t curve, called the "inflection point." This inflection point, $t_{infl}$, is indicated by the point of maximum slope on the T-t curve (i.e., peak-slope time) and is related to the characteristic time, $T_C$, by the following equation:

$$t_{infl} = 0.9055 \, T_C \qquad \text{EQU. 2}$$

This relationship between the inflection point and the characteristic time, as expressed by EQU. 2 above, is precise to approximately 1% for one-dimensional (1-D), as well as two-dimensional (2-D), heat flow analysis. Once an inflection point, $t_{infl}$, is determined from the T-t response, a relative thickness, L, of the object can be determined from EQU. 1 using the known thermal diffusivity, α, of the material and the actual value of $T_C$ from EQU. 2.

In this regard, a more detailed discussion of the heat-flow invariant relationship between the peak-slope time (inflection point) and the material "characteristic time" as defined above may be found in the *Review Of Progress In Quantitative Nondestructive Evaluation*, in an article by Ringermacher et al., entitled "Towards A Flat-Bottom Hole Standard For Thermal Imaging", published May 1998 by Plenum Press, New York, which is incorporated herein by reference.

Unfortunately, the above mentioned apparatus and method of U.S. Pat. No. 5,711,603 to Ringermacher et al. only produces "relative" depth measurements. It can not be used to obtain a quantitative value for the actual thickness of a metal object at a desired point. Consequently, an improved method of conducting IR transient thermography and processing the acquired data which would permit a determination of the actual thickness of metal objects was needed. One such method and apparatus is disclosed in a commonly assigned co-pending U.S. patent application (Ser. No. 09/292,886) of Ringermacher et al. filed Apr. 4, 1999. Basically, the arrangement disclosed therein utilizes a focal-plane array camera for IR image data acquisition and high-power flash lamps to rapidly heat the surface of a desired examined object along with a slab standard reference object composed of similar material and having portions of known thickness (a "thermally thick" section of the examined object may optionally be used as an "infinite half-space" thermal reference). The flash-lamp are fitted with spectrally tuned optical filters that minimize long-wave IR "afterglow" emissions and reduce background radiation effects which affect the accuracy of thermal measurements. A predetermined number of IR image frames are acquired and recorded over a predetermined period of time after firing the flash-lamps to develop a temperature-time (T-t) history of the object surface (and the reference standard). Contrast versus-time data is then developed for each pixel in the image to determine object thickness at a location corresponding to the pixel position.

In the above described method, contrast-time data is developed by subtracting temperature-time data of the slab reference standard (or temperature-time data of a thermally thick "deep" reference region of the object) from the temperature-time data of each pixel. Unfortunately, this method suffers from the disadvantage that it may introduce some degree of error when imaging objects that have varying surface uniformity. Moreover, it requires the presence of a slab standard in the image or the use of temperature-time data from a deep reference region on the object—assuming such a reference region is available. In addition, a special coating must usually be applied to the surface of the object (and the slab standard) prior to IR imaging to enhance optical absorption and improve surface uniformity.

DISCLOSURE OF THE INVENTION

The present invention relates to a nondestructive testing method and apparatus for determining and displaying the actual thickness of an object through the use of high speed infrared (IR) transient thermography. An improved high-speed IR transient thermography analysis approach is utilized to accurately measure the thickness of an object and provide a visual coded display indicative of its cross-sectional thickness over a desired area of the object. A salient feature of this improved approach is the use of a Fast-Fourier Transform resonance function to determine thickness. One beneficial aspect is that the transient thermography method of the present invention does not require the presence of a reference slab standard in the image or a usable reference region on the examined object. In addition, there is no need for special surface preparations or special surface coatings to enhance optical absorption or improve surface uniformity of the object being examined.

Basically, the present invention provides a method and apparatus for analyzing the Real and Imaginary components of the Fast Fourier Transform (FFT) of a temperature-versus-time (T-t) response curve of a rapidly heated object to obtain a frequency value that is directly related to the particular characteristic time, $T_C$, of transit for a thermal pulse through the object. Once the characteristic time is known, it can be used to compute a quantitative value for the thickness, L, between two surfaces of the object at a desired point according to EQU. 1 above. The T-t response is initially determined from thermal data acquired from successive IR camera image frames over a predetermined observation period—preferably obtained from same-side ("front-side") observations of the object. (Ideally, this observation period is at least somewhat longer than an anticipated characteristic time as determined from EQU. 1 above and an estimation of the thickness of the object being evaluated).

Essentially, the acquired thermal data is assembled to form an individual T-t response curve for each pixel in the image. The T-t response curve data associated with each pixel is then normalized and a Fast Fourier Transform (FFT) is performed to convert the data to the frequency domain. The Real component (or alternatively the Imaginary component) of the complex FFT is then analyzed to locate the inflection point of the T-t response in the frequency domain. The frequency value at this inflection point is related to the thermal characteristic time, $T_C$, according to the relationships given by EQU. 3 and EQU. 4 below:

$$T_C f_{Re} = 0.372 \qquad \text{EQU. 3}$$

$$T_C f_{Im} = 0.748 \qquad \text{EQU. 4}$$

where $f_{Re}$ is the Real component of the Fast Fourier Transform at the inflection point, and $f_{Im}$ is the Imaginary component of the Fast Fourier Transform at the inflection point, of the T-t response data associated with each pixel.

The Real component of the FFT of the T-t response data is a "resonance function"—operating much like a "thermal absorption" function in the frequency domain—whose frequency half-width at the inflection point is directly related to the characteristic time, $T_C$. Similarly, the Imaginary component of the FFT of the T-t response data is a "peaked function"—operating much like a "thermal dispersion" function in the frequency domain—whose frequency peak, $f_{Im}$, is also directly related to the characteristic time, $T_C$. Accordingly, the location of the inflection point in the frequency domain, and hence determination of the characteristic time, is accomplished either by identifying the peak of the derivative function of the Real component of the FFT or by identifying the peak value of the Imaginary component of the FFT.

As illustrated in FIG. 1, the apparatus of the present invention includes an imaging system comprising one or more high power flash lamps fitted with special optical filters, an IR sensitive focal-plane array camera for data acquisition and a display monitor. A computer system controls the imaging system, records and analyzes surface temperature data acquired via the IR camera and provides a color or gray pattern-keyed image on the display monitor that accurately corresponds to thickness of the object.

The acquisition of surface temperature data is initiated by firing the flash-lamps to illuminate the surface of the object. Spectrally tuned optical filters are used to absorb and/or reflect all 3–5 micron IR radiation back into the flash-lamp(s). This prevents undesirable long-wave IR "afterglow" emissions—typically generated by overheated metallic elements in the flash-lamps after the lamps are extinguished—from reaching the object or the camera.

A predetermined number of image frames are then recorded over a period of time after the flash lamps are fired. Each recorded image frame being made up of a predetermined n×m array of image pixels whose intensity correlate to the surface temperature of the object at the time the frame data was acquired—each pixel having an (x,y) location designation within the image frame that corresponds to a particular resolution element. The recorded IR image data is then used to develop the temperature-time (T-t) history for every elemental region or "resolution element" over the region of interest on the object surface. Next, a "knee" point is identified in the characteristic curve formed by the historical T-t data for each of the pixels. To normalize the data for all the pixels, the T-t data curve is clipped and constant-padded just past this to produce a continuous "flat" curve portion of constant temperature value equal to the curve value at the clip point.

A mathematical derivative curve of the Real component of the FFT is then computed to identify the inflection point, $f_{Re}$, of the T-t response data in the frequency domain. The derivative curve may be accurately computed, for example, by using a three-point data sampling having a first and third sample point separation that is proportionally related to the value of the image frame-number at the second sample point. Preferably, all local "peaks" in the derivative computation are identified and filtered. (For example, a weighting function can be used to adjust the significance of any such localized peaks to best identify the actual inflection point frequency). Finally, the characteristic time, $T_C$, and thickness, L, of the object at a location corresponding to each pixel is quantitatively determined according to EQU 1 and EQU 3.

Alternatively, the peak in the imaginary component of the FFT can be used to identify the inflection point, $f_{Im}$, of the T-t response data in the frequency domain. In this case, the peak can be readily determined by any conventional computational method. The characteristic time, $T_C$, and thickness, L, of the object at a location corresponding to each pixel is then quantitatively determined according to EQU 1 and EQU 4.

BRIEF DESCRIPTION OF THE DRAWINGS

The purpose and advantages gained by the present invention will be understood by careful study of the following detailed description of the presently preferred embodiment with particular reference to the accompanying drawings.

BEST MODE FOR CARRYING OUT THE INVENTION

Figure 1:
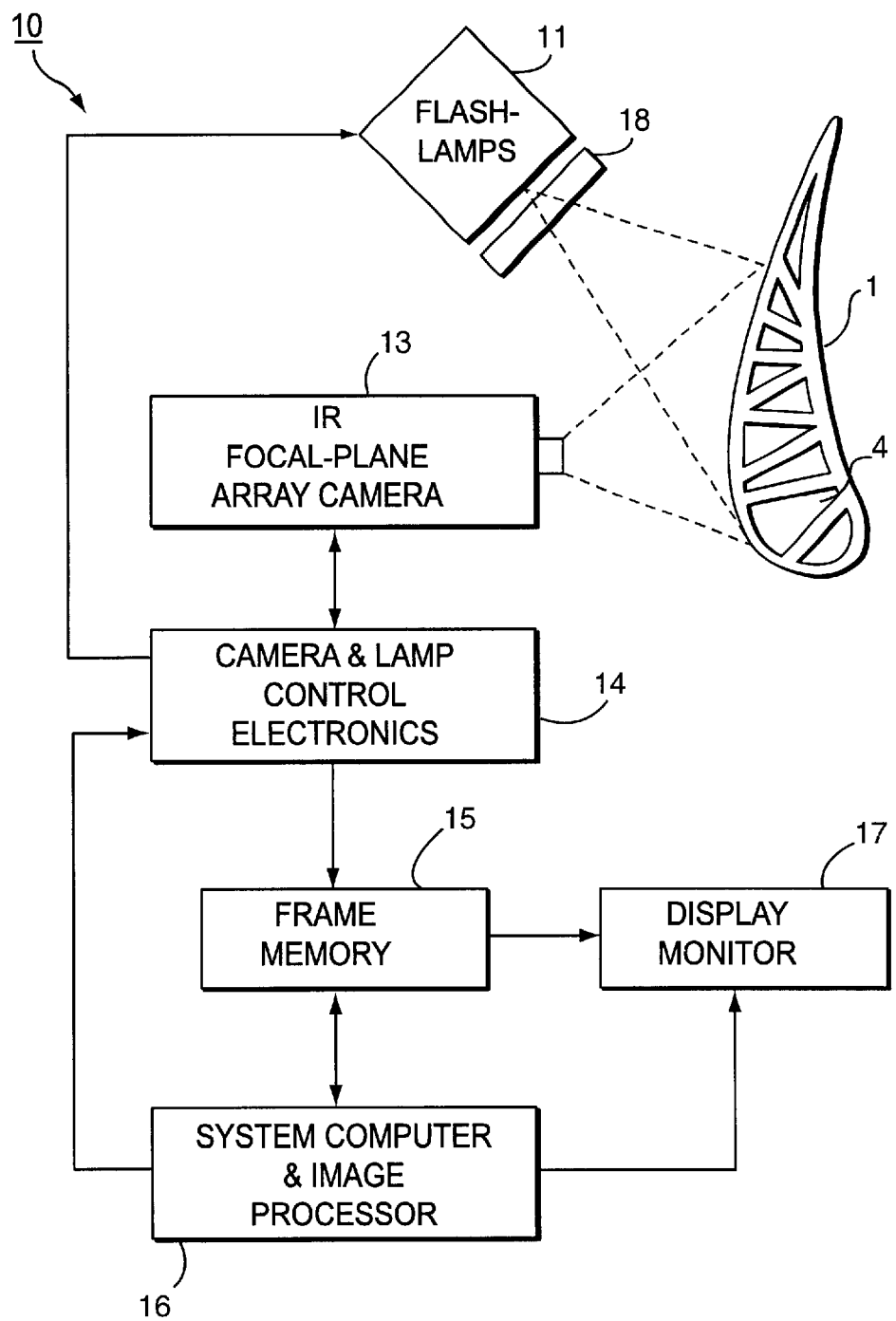
FIG. 1 is schematic diagram illustrating an example infrared transient thermography system arrangement for determining and displaying the actual thickness of an object in accordance with the present invention.

FIG. 1 illustrates an example IR transient thermography system 10 for determining and displaying the thickness of an object, e.g., a metal turbine airfoil 1 having intentional voids 4. For the purposes of the following discussion, the "thickness" of an object refers to a front wall or surface thickness in the context of a hollow or semi-hollow object (i.e., an object having an intentional void).

As shown in FIG. 1, a flash-lamp heat-pulse source 11 is used to rapidly heat the surface of the object being measured. One suitable arrangement for flash-lamp heat-pulse source 11 would be, for example, a set of four or eight high-speed, high output power photographic flash-lamps, each capable of about 4.8 Kilo-joules output and having individual power supplies (such as, for example, flash-lamps manufactured by Speedotron, Corp. in Chicago, Ill.).

Since metals have a significantly faster rate of heat conduction than non-metals, the characteristic times for heat flow in metals are much faster than those of, for example, plastic or composite materials. Consequently, in attempting to adapt conventional IR thermography—which ordinarily is limited to non-metals—to metals, a sharp cutoff in the applied heat is needed. In order to obtain this, a 3–5 micron reflective filter 18 is used between (covering) flash-lamps 11 and object of interest 1 so as to prevent exposing the object to residual heat as the flash-lamps cool down after exposure.

In practice, one or more filters may be used (e.g., one per each flash-lamp). These filters act to prevent direct long wave radiation—typically generated from the "afterglow" of overheated metallic elements in the flash-lamps—from ever leaving the flash-lamps and impinging on the target or otherwise reflecting back into focal-plane array camera 13. Such primary afterglow radiation from flash-lamps 11 competes and can interfere with the long-wave IR emissions from the targeted object during early thermal data acquisition, thus obscuring the true target-generated IR radiation and reducing ultimate image contrast and quality. Thus, the use of these special filters produces a sufficiently sharp heat pulse to enable the shorter heat travel time in metal to be detected.

In the example embodiment depicted in FIG. 1, flash-lamp filter 18 is composed of Pyrex™, fused quartz, BK7™, or other optical material that is transparent to visible and UV light and is coated on the flash-lamp facing side with an infrared-reflective coating to reflect all radiation in the 3–5 micron range back into the flash-lamps. (Optical glass and coated filters may be acquired or specially manufactured by a general scientific optics and optical glass manufacturer such as, for example, Oriel in Stratford, Conn.).

Surface temperature measurements of a heat-pulse illuminated object, 1, are acquired using a infrared (IR) sensitive imaging system comprising an IR sensitive focal-plane array camera 13 (e.g., a Radiance HS infrared camera may be available from Amber Engineering—a Raytheon Company—located in Goleta, Calif.), control electronics 14, frame data memory 15, control computer/image processor 16 and display monitor 17.

Acquisition of thermal data is preferably initiated at the time of flash lamp firing either by optical triggering or by other suitable means. Flash-lamp firing is controlled via conventional flash-lamp electronics 14 managed by conventional video frame acquisition software running on system computer 16 (such as provided by the ImageDesk™ frame acquisition system from Amber Corp. or other conventional frame acquisition and flash-lamp control software, for example, such as commercially available from Thermal Wave Imaging Inc. in Lathrup Village, Mich.).

The system control computer/image processor 16 is a specially programmed general purpose digital computer that is capable of peripheral equipment control and communication functions in addition to digital image processing and display in accordance with the method of the present invention. System computer 16 controls camera and lamp electronics 14 and frame data memory 15 to acquire a predetermined number of successive thermal image frames of the object surface which are stored in memory 15 for future analysis.

Preferably, before beginning the thermal imaging process, IR camera 13 is first calibrated using a "full-field" dual-image calibration technique as now described. This calibration technique basically employs two "black-body" (BB) image calibration references: (1) a BB "cold" source using a room-temperature flat-black plate and (2) a BB "hot" source using a heated flat-black plate. For example, for acquiring the BB "cold" source calibration image, a flat-black painted box enclosing the room-temperature flat-black plate, arranged at a 45° angle to the camera lens, is placed directly in front of the lens. For acquiring the BB "hot" source calibration image, the camera lens is placed into the same flat-black painted box unit after heating the flat-back plate—nominally to about 10° C above ambient—such that the camera images the heated plate over its full field. Although the above described dual-image calibration technique is preferred, any calibration technique that maximizes uniformity within the image field—which is important for high contrast imaging and obtaining improved thermal accuracy—can be used.

Each image frame acquired during the imaging process consists of N×N pixels—each pixel corresponding to a resolution element on the object surface—where N is typically either 128 or 256 depending on the resolution and accuracy desired. Each pixel occupies about two bytes of storage memory and may be represented, for example, by a 12-bit or larger binary number. The stored image frames are sequentially identified with increasing frame-number values which together serve to provide a historical record of the temperature vs. time (T-t) characteristics of a front surface of object 1 for a predetermined period after being struck by the heat impulse imparted by flash lamp 11.

During evaluation of a metal object, after control computer 16 triggers the firing of flash-lamp(s) 11, image data frames are acquired from camera 13 and the IR intensity at each resolution element on the image is digitally recorded and stored in frame data recorder 15. Data acquisition continues over a predetermined number of sequential image frames that are sufficient to acquire a meaningful T-t history over a duration of at least one estimated "characteristic time" for the material of the object. The total number of image frames acquired may vary depending on the accuracy and image resolution desired and can be as high as 550 frames per second of data acquisition.

Frame data recorder 15 may be a conventional digital memory internal to processor 16 or any suitable video frame data storage device accessible by processor 16. Each successive thermal image frame acquired is assigned an increasing value frame-number, Z, corresponding to the passage of real time. The resulting data frame "stack" is then analyzed using a one-dimensional heat flow analysis approach, as outlined above. In accordance with this approach, the method of the present invention takes advantage of a known thermal invariance property—evidenced in the temperature vs. time (T-t) history of each image pixel over successive IR image frames—that relies on identifying the location of an "inflection point" or peak-slope time, i.e., the point in time of maximum slope on the T-t data curve.

Figure 2:
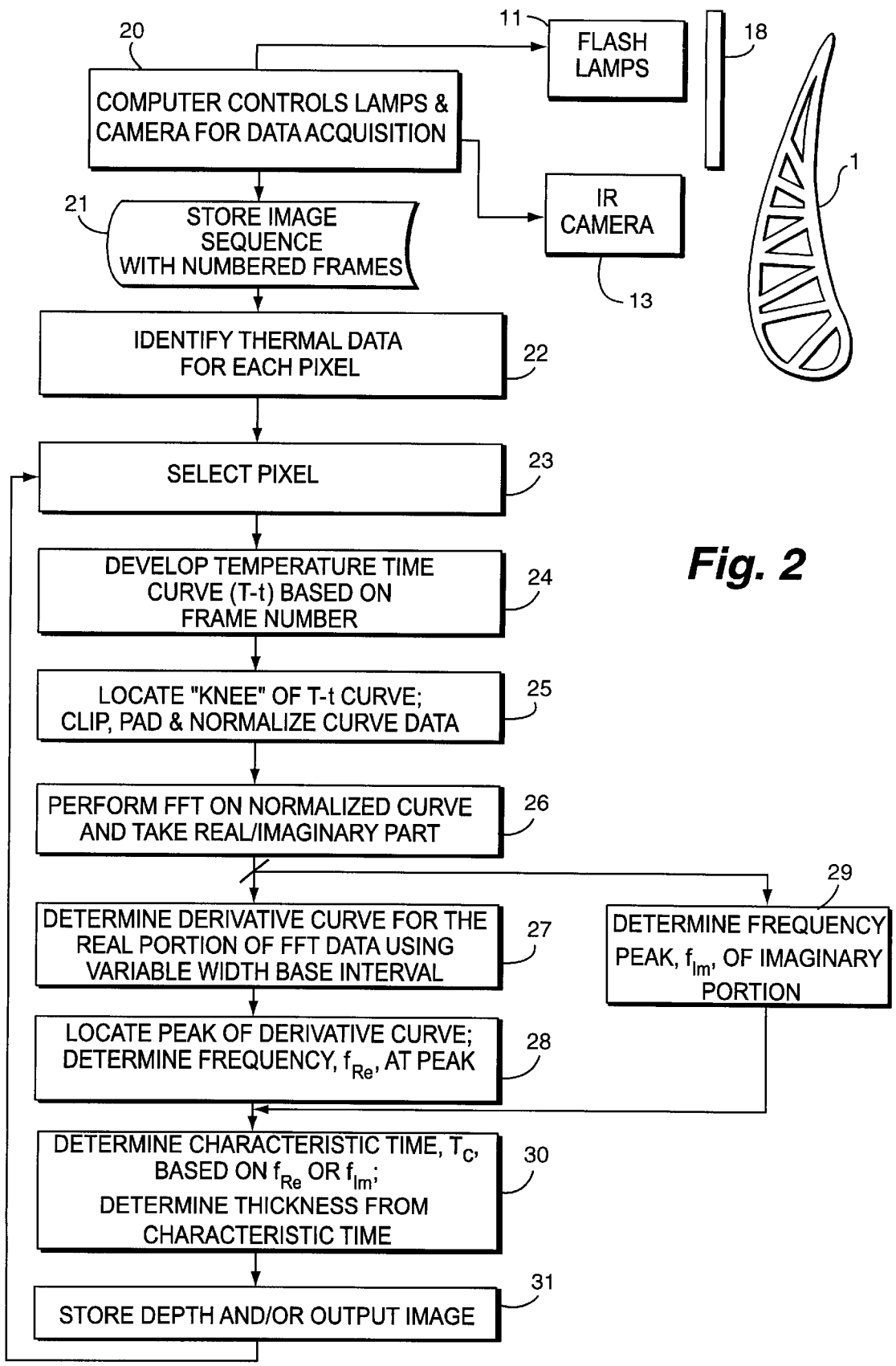
FIG. 2 is a flowchart illustrating the process of infrared image data acquisition and analysis as performed by the system of FIG. 1 in accordance with the present invention.

Referring now to FIG. 2, a flow diagram is presented that illustrates example processing steps for conducting transient IR thermography using thermal resonance imaging techniques of the present invention. These steps may be implemented, for example, by appropriately programming computer 16 (FIG. 1) using known conventional programming languages/techniques.

Initially, as indicated at block 20, a region of interest on object 1 is identified (i.e., the IR camera is focused to capture the region of interest) and a system operator selects/inputs information concerning relevant parameters for examining the object such as, for example, a thermal diffusivity coefficient for the object. Next, as indicated at block 20 in FIG. 2, the system control computer instructs the flash-lamp electronics to fire flash-lamps 11 and initiate image frame data acquisition from the focal plane array IR camera 13. Data acquisition proceeds over a predetermined number of sequential image frames and then, as indicated at 21, the image sequence is stored in frame memory 15 after identifying each acquired image frame with a sequential frame-number, Z.

Next, as indicated at 22, thermal data is identified to each pixel in the thermal image corresponding to each resolution element location over the region of interest on the surface of the object for all of the sequential frames. A pixel is then selected for evaluation, as indicated at 23. Next, as indicated at 24, T-t curve data is developed for each pixel using the frame-number as the temporal ordinate. Also, a time (frame-number) of the initial IR heating "flash" is identified and a first unsaturated data frame is identified.

Next, as indicated at 25, a "knee" portion is identified in each characteristic T-t data curve for each of the pixels. The T-t data curve of each pixel is then clipped and constant-padded just past this "knee-portion" to produce a continuous "flat" curve portion having a constant temperature value equal to the T-t data value at the clip point. Preferably, a data-clipping point, $T_{Cp}$, is selected that is slightly greater than the range of time values nominally corresponding to the knee-portion of the curve and, at least, greater than a time $t=L^2/\pi^2\alpha$. The exact value or point in time of the selected clipping-point, $T_{Cp}$, is not critical, however, its selection will affect the ultimate quality of any images produced. Accordingly, selection of an appropriate clipping point is best determined through an empirical comparison of images developed using a variety of nearby clipping points selected from a region along the characteristic T-t data curve near the end of the identified knee-portion, but of at least a value greater than a time $t=L^2/\pi^2\alpha$. In addition, to normalize the data for all of the pixels in the image, the T-t curve for each pixel is offset by a selected bias value such that the "flat" portion corresponding to the constant temperature value is equal to zero.

Next, as indicated at 26, a Fast Fourier Transform (FFT) is performed on the normalized curve data and either the Real or Imaginary component portion of the resulting transform data may be then analyzed to identify the inflection point in the frequency domain. If the Real component portion is selected, as indicated by blocks 27 and 28, a mathematical derivative of the Real component of the FFT is first determined. To compute the derivative data, a variable width base interval may be used. For example, for any selected point along the Real component data curve, the base interval for computing the derivative is made proportional to the square-root of the IR image frame-number, Z.

Next, at step 28, all local peaks in the derivative curve are identified and a significance/weighting filter is used to assess the proper peak to interpret as the inflection point. For example, a list of all peak frames and amplitudes may be maintained in computer memory. By applying a predetermined appropriate weighting function to this list, it is possible to adjust the significance of each local peak so that, for example, noise effects arising early in the data acquisition time may be effectively discounted. The peaks are then sorted according to decreasing significance/weight and the peak having the greatest weight value (i.e., the most significant) is selected as indicative of the inflection point. As indicated at step 30, the frequency, $f_{Re}$, at this peak is then used to quantitatively determine characteristic time, $T_C$, and thickness, L, of the object at a location corresponding to each pixel according to equations EQU 1 and EQU 3 (above).

Alternatively, in lieu of steps 27 and 28, a peak in the Imaginary component portion of the FFT of the T-t response data can also be used to identify the inflection point in the frequency domain, as indicated at step 29. In this case, the peak in the Imaginary component can be determined through ordinary conventional computational methods. As indicated at step 30, the frequency, $f_{Im}$, at this peak is then used to determine the characteristic time, $T_C$, and thickness, L, of the object at a location corresponding to each pixel according to equations EQU 1 and EQU 4 (above).

Finally, at step 31, the computed thickness value, L, is stored in memory and used to build a color-mapped or gray-scale image of the region of interest on the object surface for display or print—each color or gray shade corresponding to a particular thickness. The next pixel is then selected, as indicated by the arrow to step 23, and the above steps are reiterated for each pixel comprising the IR image. By conducting a transient thermography analysis using the above described steps for thermal data acquisition and analysis in conjunction with the above described apparatus, wall thickness values may be accurately obtained for even closely spaced back-wall or internal structures that form a part of, or are connected to, the tested object—e.g., like the rib-like structures often found in turbine air foils such as pictured in FIG. 1. If desired, the input and selection of various parameter values such as diffusivity constant, data analysis starting point and color mapping range may also be automated through conventional programming of the system control computer.

Figure 3:
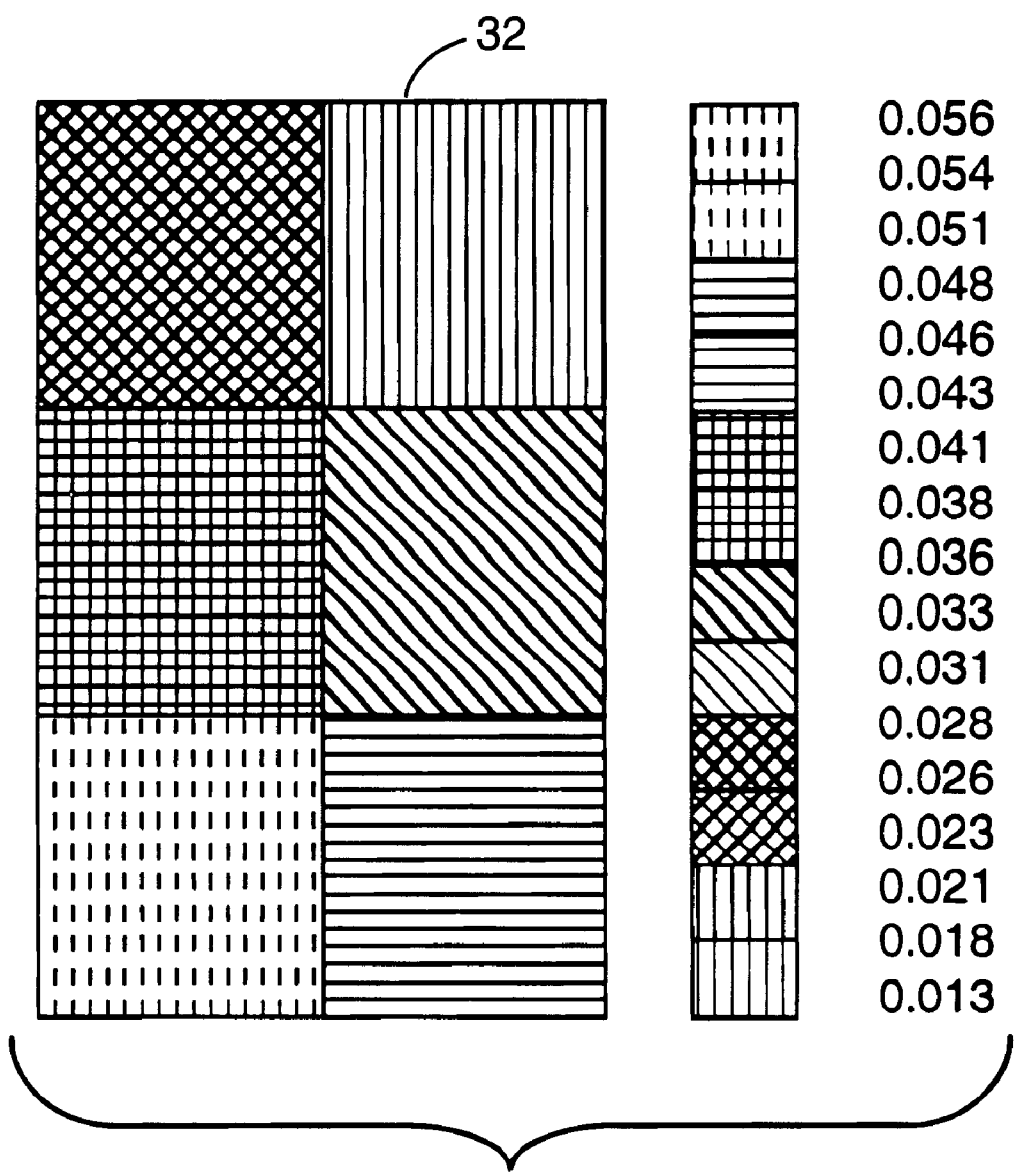
FIG. 3 is a diagram of an example IR transient thermography image display of a multi-tiered object.

Referring finally now to FIG. 3, a diagram of an IR transient thermography display image for a multi-tiered object block is shown. The object block, 32, depicted in FIG. 3 has six square sections of different thickness. The thickness of each of the six sections is indicated by a different color or gray tone shade in the generated image (shown here as different cross-hatchings) which correspond to a like color or shade in a bar-scale thickness key displayed at the right of the image. In this example, the barscale includes indicia of thickness ranging from 0.013 to 0.056 inches, but one skilled in the art will appreciate that a displayed barscale having a different range of thickness values could also be readily implemented in the present invention.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for determining a thickness of an object having a surface which can be visualized as an array of pixels, comprising the steps of:
   a) rapidly heating the surface of an object;
   b) recording pixel intensity in a sequence of IR images, each image having an assigned sequential frame-number related to time elapsed since heating the object surface in step (a);
   c) developing temperature-versus-time (T-t) data corresponding to a pixel in the sequence of image frames based on frame-number value;
   d) transforming the T-t data developed in step (c) into complex frequency-domain data having Real and Imaginary components; and
   e) determining a thickness value for a point on the object corresponding to a pixel based at least upon the complex frequency domain data and a heat-flux pulse migration characteristic time for the object.

2. The method of claim 1 wherein the object is heated by using a flash lamp device.

3. The IR transient thermography method of claim 1 wherein the step of developing temperature-versus-time (T-t) data corresponding to a pixel further includes the step of normalizing the T-t data by:
   i) identifying a knee-portion in the T-t data and selecting a dataclipping point in time being greater than a range of time values corresponding to the knee-portion;
   ii) clipping the T-t data at the data-clipping point identified in step (i) and constant-padding the T-t data for time values greater than the data-clipping point with T-t data values equal to a temperature value at the data-clipping point; and
   iii) offsetting the T-t data by a bias value such that the T-t data for time values greater than the data-clipping point are equal to zero.

4. The IR transient thermography method of claim 1 wherein the transforming of T-t data to produce complex frequency-domain data is accomplished by computing a Fast Fourier Transform of the T-t data.

5. The IR transient thermography method of claim 3 wherein the step of selecting a data-clipping point, $T_{Cp}$, further comprises the step of making an empirical comparison of images developed by using a variety of nearby clipping points selected from a region along the characteristic T-t data curve near the end of the identified knee-portion, but of at least a value greater than a time $t=L^2/\pi^2\alpha$, where L is the thickness (cm) of the object and $\alpha$ is the thermal diffusivity (cm$^2$/sec) of the material.

6. An infrared (IR) transient thermography method for determining a thickness of an object using an IR sensitive focal-plane array camera, comprising the steps of:

a) acquiring pixel intensity data from a sequence of IR image frames of the object, each image frame comprising a plurality of pixels and having an assigned sequential frame-number related to elapsed time;

b) developing temperature-versus-time (T-t) data corresponding to a pixel from pixel intensity data acquired in step (a) based on frame-number value for a sequence of image frames;

c) performing a Fast Fourier Transform on the temperature-versus-time data developed in step (b) to produce frequency-domain data having Real and Imaginary components;

d) determining derivative data of a Real component portion of the frequency-domain data obtained in step (c);

e) identifying a peak frequency value, $f_{Re}$, in the derivative data; and f) determining a thickness value, L, based on the peak frequency value, $f_{Re}$, identified in step (e).

7. The IR transient thermography method of claim 6 wherein a thickness value, L, is determined from a quantitative value for $f_{lm}$ according to the following relationship:

$$(L^2/\pi^2\alpha)f_{lm}=0.093$$

where L is the thickness (cm) of the object and $\alpha$ is the thermal diffusivity (cm$^2$/sec) of the material.

8. The IR transient thermography method of claim 6 wherein a thickness value, L, is determined from a quantitative value for $f_{Re}$ according to the following two relationships:

$$T_C=4L^2/\pi^2\alpha$$

and $$T_Cf_{Re}=0.372$$

where $T_C$ is a heat-flux pulse migration characteristic time value for an object, L is the thickness (cm) of the object and $\alpha$ is the thermal diffusivity of the object.

9. The method of claim 6 wherein the object is heated using a flash lamp device.

10. The IR transient thermography method of claim 6 wherein the step of developing temperature-versus-time (T-t) data corresponding to a pixel further includes the step of normalizing the T-t data by:

i) identifying a knee-portion in the T-t data and selecting a data-clipping point in time being greater than a range of time values corresponding to the knee-portion;

ii) clipping the T-t data at the data-clipping point identified in step (i) and constant-padding the T-t data for time values greater than the data-clipping point with T-t data values equal to a temperature value at the data-clipping point; and iii) offsetting the T-t data by a bias value such that the T-t data for time values greater than the data-clipping point are equal to zero.

11. The IR transient thermography method of claim 10 wherein the step of selecting a data-clipping point, $T_{Cp}$, further comprises the step of making an empirical comparison of images developed by using a variety of nearby clipping points selected from a region along the characteristic T-t data curve near the end of the identified knee-portion, but of at least a value greater than a time $t=L^2/\pi^2\alpha$, where L is the thickness (cm) of the object and $\alpha$ is the thermal diffusivity (cm$^2$/sec) of the material.

12. An infrared (IR) transient thermography method for determining a thickness of an object using an IR sensitive focal-plane array camera, comprising the steps of:

a) acquiring pixel intensity data from a sequence of IR image frames of the object, each image frame comprising a plurality of pixels and having an assigned sequential frame-number related to elapsed time;

b) developing temperature-versus-time (T-t) data corresponding to a pixel from pixel intensity data acquired in step (a) based on frame-number value for a sequence of image frames c) performing a Fast Fourier Transform on the temperature-versus-time data developed in step (b) to produce frequency-domain data having Real and Imaginary components;

d) determining a peak frequency value, $f_{lm}$, of an Imaginary component portion of the frequency-domain data obtained in step (c); and f) determining a thickness value, L, based on the peak frequency value, $f_{lm}$, identified in step (d).

13. The IR transient thermography method of claim 12 wherein a thickness value, L, is determined from a quantitative value for $f_{lm}$ according to the following relationship:

$$(L^2/\pi^2\alpha)f_{lm}=0.187$$

where L is the thickness (cm) of the object and $\alpha$ is the thermal diffusivity (cm$^2$/sec) of the material.

14. The IR transient thermography method of claim 12 wherein a thickness value, L, is determined from a quantitative value for $f_{lm}$ according to the following two relationships:

$$T_C=4L^2/\pi^2\alpha$$

and $$T_Cf_{lm}=0.748$$

where $T_C$ is a heat-flux pulse migration characteristic time value for an object, L is the thickness (cm) of the object and $\alpha$ is the thermal diffusivity of the object.

15. The method of claim 12 wherein the object is heated using a flash lamp device.

16. The IR transient thermography method of claim 12 wherein the step of developing temperature-versus-time (T-t) data corresponding to a pixel further includes the step of normalizing the T-t data by:

i) identifying a knee-portion in the T-t data and selecting a data-clipping point in time, $T_{Cp}$, greater than a range of time values corresponding to the knee-portion;

ii) clipping the T-t data at the data-clipping point identified in step (i) and constant-padding the T-t data for time values greater than the data-clipping point with T-t data values equal to a temperature value at the data-clipping point; and iii) offsetting the T-t data by a bias value such that the T-t data for time values greater than the data-clipping point are equal to zero.

17. The IR transient thermography method of claim 16 wherein the step of selecting a data-clipping point, $T_{Cp}$, further comprises the step of making an empirical comparison of images developed by using a variety of nearby clipping points selected from a region along the characteristic T-t data curve near the end of the identified knee-portion, but of at least a value greater than a time $t=L^2/\pi^2\alpha$, where L is the thickness (cm) of the object and $\alpha$ is the thermal diffusivity (cm$^2$/sec) of the material.

18. An apparatus for determining a thickness of an object having a surface which can be visualized as an array of pixels, comprising:

a heat source for rapidly heating the surface of an object;

a means for recording pixel intensity in a sequence of IR images;

a means for determining temperature-versus-time data from recorded pixel intensity based on a frame-number value assigned to an IR image;

a means for transforming temperature-versus-time data into complex frequency domain data; and a means for determining a thickness of an object based upon the complex frequency domain data and a transient thermal pulse characteristic time for the object.

* * * * *